United States Patent
Missout et al.

[11] Patent Number: 5,825,956
[45] Date of Patent: Oct. 20, 1998

[54] FIBRE-OPTIC CABLE HAVING ENHANCED CRUSHING STRENGTH

[75] Inventors: Bernard Michel Missout, Ivry sur Seine; Herve Heude, Lyons; Pierre Laroche, Baudille de la Tour, all of France

[73] Assignee: Cables Pirelli, France

[21] Appl. No.: 822,574

[22] Filed: Mar. 19, 1997

[30] Foreign Application Priority Data

Feb. 29, 1996 [FR] France ................................... 96 02545

[51] Int. Cl.⁶ ................................................... G02B 6/44
[52] U.S. Cl. ........................................... 385/102; 385/112
[58] Field of Search .................................... 385/100, 101, 385/102–114

[56] References Cited

U.S. PATENT DOCUMENTS

| | | | |
|---|---|---|---|
| 3,941,157 | 3/1976 | Barnett | 138/115 |
| 4,761,053 | 8/1988 | Cogelia et al. | 385/100 X |
| 5,031,997 | 7/1991 | Redford et al. | 385/107 |
| 5,319,730 | 6/1994 | Räsänen et al. | 385/14 |

FOREIGN PATENT DOCUMENTS

| | | | |
|---|---|---|---|
| 7404872 | 9/1975 | France | G02B 5/14 |
| 9201962 | 2/1992 | WIPO | G02B 6/44 |

*Primary Examiner*—Phan T. H. Palmer
*Attorney, Agent, or Firm*—Brooks Haidt Haffner & Delahunty

[57] ABSTRACT

The cable (1) comprises a plurality of optical fibre micromodules (2) grouped together inside an external sheath (4). The external portion of the latter has four bosses (5) moulded integral therewith and which extend along the entire length of the cable and form, along the generating lines of the cable, four diametrically opposed ribs. These bosses, by creating a special arrangement for application to the cable of compressive forces, produce an improvement in crushing strength.

5 Claims, 1 Drawing Sheet

FIBRE-OPTIC CABLE HAVING ENHANCED CRUSHING STRENGTH

FIELD OF THE INVENTION

The invention relates to fibre-optic cables and, more specifically, to cables the structure and shape of which are such that their crushing strength is quite markedly improved, in particular by comparison wit cables having a circular cross-section of a conventional design.

DESCRIPTION OF RELATED ART

Fibre-optic cables are well known and have developed rapidly over the last few years, particularly in the field of telecommunications, owing to the considerable transmission potential of optical fibres of very small dimensions. Those fibres nonetheless have to be mechanically protected, by the structure of the cable, from the stresses associated with the radial forces applied to the cable, such as crushing, impact, etc. Cable structures enclosing these fibres have thus been developed to protect them mechanically according to the environments in which they are located.

Known fibre-optic cables have a variety of structures. There is known, for instance, a type of tube-equipped cable comprising a central reinforcement, surrounded by a plurality of helically or pseudo-helically wound tubes enclosing a bundle of optical fibres capable of moving within the tubes. This ability of the fibres to move within the tubes compensates for the variations in the length of cable due to thermal or tensile stresses. This structure is, however, too voluminous by comparison with the real space taken up by the fibres it contains and it is unsuitable, for example, for distribution cables in an urban network in which the object is to obtain an optimal ration the number of fibres to the diameter of the cable.

It is thus preferred to use cables with a low expansion coefficient, wherein the fibres are, for example, disposed in bundles (round or flat ribbon micro-modules), the bundles being disposed practically without clearance between them in the inner cylindrical cavity of the cable.

A good ratio of the number of fibres to the outside diameter of the cable and thus be obtained. The cross-section of the cables is circular and the sheaths of the cables may possibly incorporated metallic or non-metallic reinforcements, which may be two in number, and which extend along two diametrically opposed generating lines. By reason of the very small radial clearance that remains between the fibres and the inner cavity of the cable, when crushing forces are applied or in the event of impacts, the deformation of the inner cavity containing the fibres that is induced exerts inadmissible compressive stress on the said fibres, leading to additional weakening or even failure.

The sheath therefore has to be reinforced to limit its deformation as far as possible when the aforementioned stresses are applied.

The solutions adopted to reduce these deformations, such as the use of metallic reinforcements, materials having a high modulus of elasticity, wall thickening, etc., have drawbacks, however.

SUMMARY OF THE INVENTION

The Applicant has thus applied itself to finding a solution to this problem to enable an optical cable, whatever the environment in which it is located, to possess increased resistance to the stresses to which it might be subjected and particularly cable of withstanding any localized crushing or impacts that it might be exposed to, for instance at the time of cable laying operations.

One main object of the present invention thus resides in an optical cable possessing crushing strength, comprising a plurality of optical fibres located inside a sheath, an optical cable in which the external part of the sheath possesses four bosses moulded integrally therewith, which extend over the entire length of the cable, and form along the generating lines of the cable four diametrically opposed ribs.

BRIEF DESCRIPTION OF THE DRAWINGS

Other characteristics and advantages of the invention will emerge from the following description of a non-limitative example of a form of embodiment, with reference to the figures, which represent cross-sectional views of optical cables. FIG. 2 illustrates the application of the stresses to a circular cable of conventional design.

DESCRIPTION OF PREFERRED EMBODIMENTS

Figure 1:
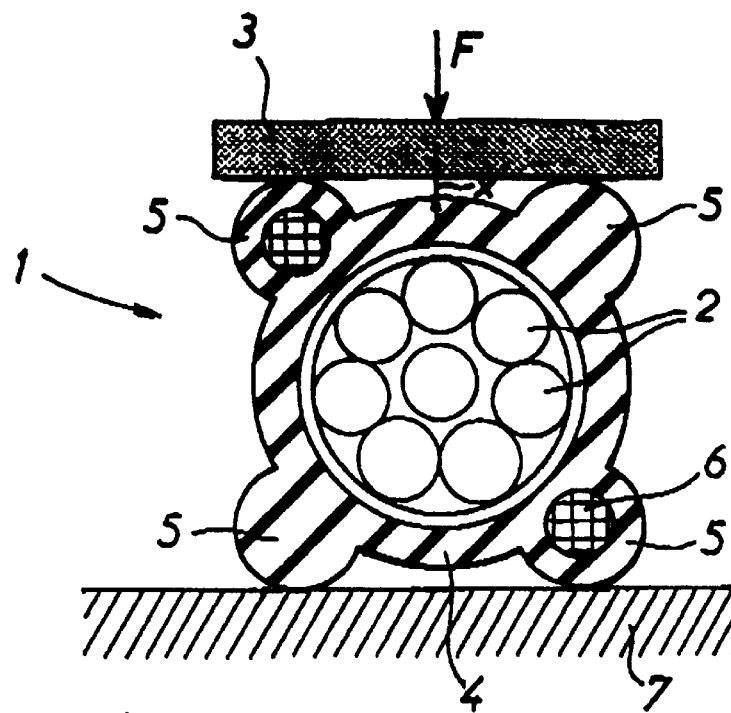
FIGS. 1 and 2 are cross-sectional views of the cable according to the invention.
Figure 2:
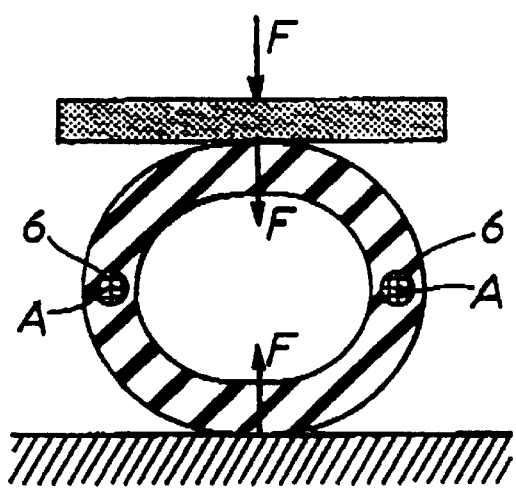

Cable 1, shown in FIG. 1, comprises in its centre a group of eight optical fibre micro-modules 2. The micro-modules are covered by an outer sheath 4.

The outer portion of sheath 4 is not circular but has, along diametrically opposed generating lines, four bosses 5 which extend over the entire length of the cable. The bosses, which are integrally moulded into the body of the sheath, form, as it were, external ribs which project in relation to a tangent to the circular portion of sheath, and which have a rounded external profile. If necessary, traction reinforcements 6 can be provided inside one or more of these bosses, the reinforcements being metallic or non-metallic, for example made of aramid resin, and being embedded in the sheath in the area of the bosses when the cable is extruded. Alternatively, traction elements or copper wires can also be housed in the bosses. These elements can serve as leads or limit the minimum radius or curvature of the cable.

This arrangement thus makes it possible to avoid making the sheath 4, one of the functions of which is to withstanding crushing, very thick. Thanks to the bosses, it is thus possible to reduce the thickness of the sheath, which reduces the weight of the cable by a corresponding amount and lowers the thermal expansion coefficient.

When a compressive stress, represented in FIG. 1 by the presence of a plate a pushed by a force F, is applied to the cable, the stable position of the cable is as shown in FIG. 1. If the stress is applied thereto along another generating line, it will automatically tip over to resume the position represented.

Figure 3:
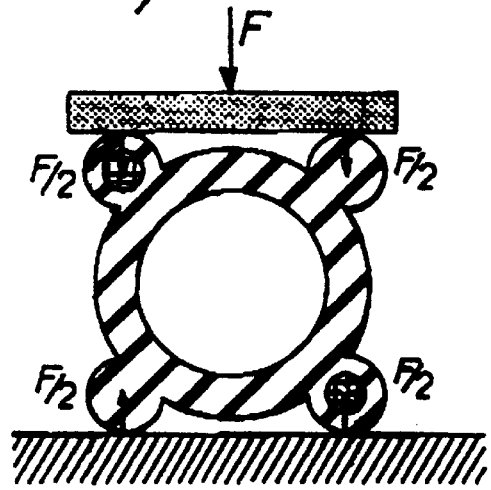

For the same sheath thickness, the case in which the stress is applied illustrated in FIG. 3 is clearly more favorable, among other positive effects, than the case shown in FIG. 3, as it produces a smaller bending moment at the inferior point. The result is, for the same stress, a deflection under loss that is smaller in the case shown in FIG. 3 that in that of FIG. 3.

Figure 4:
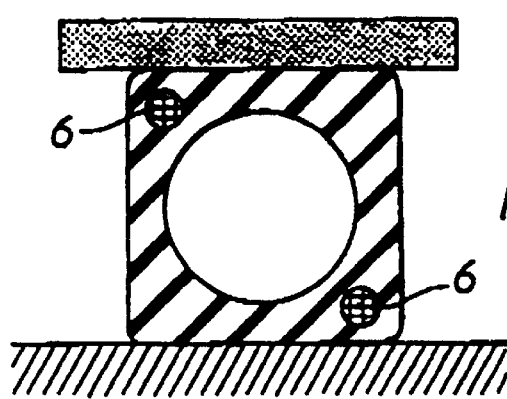
FIG. 4 diagrammatically represents an alternative form of embodiment.

According to the same principle, the external shape could be practically square, as illustrated in FIG. 4.

For maximum efficiency, distance X must be positive, or at the very least nil, as shown in FIG. 1.

We claim:

1. An optical fiber cable having improved crushing strength, said cable comprising:

a tubular plastic sheath having a length and having a wall of a predetermined inner diameter which encircles a plurality of optical fibers;

said wall having a radial thickness at four portions of the wall spaced substantially equally from each other in the circumferential direction of the wall which is greater than the thickness of the wall intermediate said portions to provide two pairs of ribs extending outwardly from said wall and lengthwise of said sheath, one pair of said ribs being diametrically opposed with respect to each other and the other pair of said ribs being diametrically opposed with respect to each other.

2. Optical cable according to claim 1, characterized in that two of the diametrically opposed ribs enclose metallic or non-metallic reinforcements.

3. Optical cable according to claim 1, characterized in that the optical fibres are grouped together in micro-modules.

4. Optical cable according to claim 1, characterized in that the optical fibres are grouped together in ribbons.

5. Optical cable according to claim 1, characterized in that at least two of the diametrically opposed ribs enclose metallic or non-metallic reinforcements which can serve as leads or limit the minimum radius of curvature of the cable.

* * * * *